US010195230B2

(12) United States Patent
Merchant et al.

(10) Patent No.: US 10,195,230 B2
(45) Date of Patent: Feb. 5, 2019

(54) BLOOD PRODUCT FROM CROCODYLIAN SPECIES AS A FEED SUPPLEMENT FOR WEANLING PIGS AND POULTRY HATCHLINGS

(75) Inventors: Mark E. Merchant, Nederland, TX (US); Frederick LeMieux, Jr., Lake Charles, LA (US)

(73) Assignee: McNeese State University, Lake Charles, LA (US)

( * ) Notice: Subject to any disclaimer, the term of this patent is extended or adjusted under 35 U.S.C. 154(b) by 2093 days.

(21) Appl. No.: 11/640,421

(22) Filed: Dec. 14, 2006

(65) Prior Publication Data
US 2008/0145444 A1    Jun. 19, 2008

(51) Int. Cl.
| A61K 35/16 | (2015.01) |
| A23K 10/24 | (2016.01) |
| A23K 50/75 | (2016.01) |
| A23K 50/30 | (2016.01) |
| A23K 50/60 | (2016.01) |

(52) U.S. Cl.
CPC .............. *A61K 35/16* (2013.01); *A23K 10/24* (2016.05); *A23K 50/30* (2016.05); *A23K 50/60* (2016.05); *A23K 50/75* (2016.05)

(58) Field of Classification Search
CPC ..................................................... A61K 35/16
USPC ....................................................... 424/442
See application file for complete search history.

(56) References Cited

U.S. PATENT DOCUMENTS

| 5,575,999 | A | 11/1996 | Yoder |
| 5,637,345 | A | 6/1997 | Lee et al. |
| 5,785,990 | A | 7/1998 | Langrehr |
| 6,004,576 | A | 12/1999 | Weaver et al. |
| 6,569,447 | B2 | 5/2003 | Kisic et al. |
| 2004/0247589 | A1 * | 12/2004 | Binah et al. ............... 424/130.1 |

FOREIGN PATENT DOCUMENTS

CN           1634147    *  7/2005  ............. A61K 35/56

OTHER PUBLICATIONS

Dill et al., 1935, Journal of Cellular and Comparative Physiology, 6, 243-254.*
Yanochko et al., 1997, Arch. Environ. Contam. Toxicol., 32, 323-328.*
Siruntawineti, J. et al., 2004, "Crocodile Blood as a Food Supplement: Its Effect on Hematological Values in Wistar Rats", 30th Congress on Science & Technology of Thailand, 3 pages.*
Odum et al., 2001, Toxicological Sciences, 61, 115-127.*
CN 1634147, 2005, Machine Translation from Google Patents, pp. 1-7.*
Sillence, et al. 1991. Cortisone arrests growth but enhances . . . J Anim Sci 69:2815-2821.
Ermer, et al. 1994. Diet preference and meal patterns of weanling pigs . . . J Anim Sci 72:1548-1554.
Kats et al. 1994. Effect of spray-dried porcine plasma on growth . . . J Anim Sci 72:2075-2081.
Thomas, et al. 1994. Effect of spray-dried porcine plasma protein on food . . . J Anim Sci 72:2690-2695.
Kats, et al. 1994. Effects of spray-dried blood meal on growth . . . J Anim Sci 72:2860-2869.
Coffey, et al. 1995. Impact of env. & antmicrcbial agents . . . J Anim Sci 73:2532-2539.
Thomson, et al. 1995. Effects of spray-dried porcine plasma protein. J Anim Sci 73:2340-2346.
Derodas, et al. 1995. Plasma protein for pigs weaned at 19 to 24 days . . . J Anim Sci 73:3657-3665.
Dritz, et al. 1995. Influence of dietary beta-glucan on growth . . . J Anim Sci 73:3341-3350.
Sensky, et al. 1996. Relationship btw. plasma ephinephrine concentration . . . J Anim Sci 74:380-387.
Luo, et al. 1996. Effect of dietary copper & fat on nutrient utilization . . . J Anim Sci 74:1888-1896.
Grinstead, et al. 2000. Effects of whey protein product . . . J Anim Sci 78:647-657.
Owusu-Asiedu, et al. 2002. Response of early-weaned pigs to spray-dried . . . J Anim Sci 80:2895-2903.
Derouchey, et al. 2002. Comparison of spray-dried blood meal . . . J Anim Sci 80:2879-2886.
Torralardona, et al. 2003. Effect of fishmeal replacement. J Anim Sci 81:1220-1226.
Owusu-Asiedu, et al. 2003. Response of early-weaned pigs to . . . J Anim Sci 81:1790-1798.
Owusu-Asiedu, et al. 2003. Response of early-weaned pigs to . . . J Anim Sci 81:1781-1789.
DeRouchey, et al. 2003. Effects of blood meal pH & irradiation on nursery . . . J Anim Sci 81:1013-1022.
Zier, et al. 2004. Use of pet food-grade poultry by-product meal . . . J Anim Sci 82:3049-3057.
Polo, et al. 2005. Efficacy of spray-drying to reduce infectivity. J Anim Sci 83:1933-1938.
Nofrarias, et al. 2006. Effects of spray-dried porcine plasma & plant . . . J Anim Sci 84:2735-2742.
Merchant, et al. 2006. Comparisons of innate immune activity . . . Comp Bio & Physi, Part B 143:133-137.
Merchant, et al. 2006. Characterization of serum complement . . . Comp Bio & Physi, Part A 143:488-493.
Compton, et al. Mar. 10, 2006. Effects of American alligator serum on growth performance of early-weaned.

(Continued)

*Primary Examiner* — Bin Shen
(74) *Attorney, Agent, or Firm* — Jones Walker LLP

(57) ABSTRACT

The present invention is a feed supplement consisting of a blood product from at least one Crocodylian species such as the American alligator (*Alligator mississippiensis*). The blood product is whole blood, hemolyzed blood, serum or plasma. The feed supplement is a liquid or solid. The feed supplement may be combined with a high nutrient feed or starter diet. The feed composition may contain 0.1% or more by weight of the feed supplement. The feed supplement is fed to weanling pigs or poultry hatchlings to increase their weight and feed intake. It is also expected to promote gut health.

8 Claims, No Drawings

(56) References Cited

OTHER PUBLICATIONS

M.N. Sillence and T.D. Etherton. 1991. Cortisone arrests growth but enhances the inductive effect of porcine growth hormone on plasma IGF-I concentrations in female rats. J Anim Sci 69:2815-2821.

P.M. Ermer, P.S. Miller, and A.J. Lewis. 1994. Diet preference and meal patterns of weanling pigs offered diets containing either spray-dried porcine plasma or dried skim milk. J Anim Sci 72:1548-1554.

L.J. Kats, J.L. Nelssen, M.D. Tokach, R.D. Goodband, J.A. Hansen, and J.L. Laurin. 1994. The effect of spray-dried porcine plasma on growth performance in the early-weaned pig. J Anim Sci 72:2075-2081.

J.E. Thomas, E.E. Jones, and E.J. Eisen. 1994. Effect of spray-dried porcine plasma protein on feed intake, growth rate, and efficiency of grain in mice. J. Anim Sci 72:2690-2695.

L.J. Kats, J.L. Nelssen, M.D. Tokach, R.D. Goodband, S.S. Dritz, J.C. Woodworth, and B.W. James. 1994. The Effects of spray-dried blood meal on growth preformance of the early-weaned pig. J Anim Sci 72:2860-2869.

R.D. Coffey and G.L. Cromwell. 1995. The impact of environment and antimicrobial agents on the growth response of early-weaned pigs to spray-dried porcine plasma. J Anim Sci 1995 73:2532-2539.

J.E. Thomson, E.E. Jones, and E.J. Eisen. 1995. Effects of spray-dried porcine plasma protein on growth traits and nitrogen and energy balance in mice. J Anim. Sci 73:2340-2346.

B.Z. deRodas, K.S. Sohn, C.V. Maxwell, and L.J. Spicer. 1995. Plasma protein for pigs weaned at 19 to 24 days of age: effect on performance and plasma insulin-like growth factor I, growth hormone, insulin, and glucose concentrations. J Anim Sci 73:3657-3665.

S.S. Dritz, J. Shi, T.L. Kielian, R.D. Goodband, J.L. Nelssen, M.D. Tokach, M. Chengappa, J.E. Smith, and F. Blecha. 1995. Influence of dietary beta-glucan on growth performance, nonspecific immunity, and resistance to *Streptococcus suis* infection in weanling pigs. J Anim Sci 73:3341-3350.

P.L. Sensky, T. Parr, R.G. Bardsley, and P.J. Buttery. 1996. The relationship between plasma epinephrine concentration and the activity of the calpain enzyme system in porcine longissimus muscle. J Anim Sci 74:380-387.

G. Luo and C.R. Dove. 1996. Effect of dietary copper and fat on nutrient utilization, digestive enzyme activities, and tissue mineral levels in weanling pigs. J Anim Sci 74:1888-1896.

G.S. Grinstead, R.D. Goodband, S.S. Dritz, M.D. Tokach, J.L. Nelssen, J.C. Woodworth, and M. Molitor. 2000. Effects of a whey protein product and spray-dried animal plasma on growth performance of weanling pigs. J Anim Sci 78:647-657.

Owusu-Asiedu, S.K. Baidoo, C.M. Nyachoti, and R.R. Marquardt. 2002. Response of early-weaned pigs to spray-dried porcine or animal plasma-based diets supplemented with egg-yolk antibodies against enterotoxigenic *Escherichia coli*. J Anim Sci 80:2895-2903.

J.M. DeRouchey, M.D. Tokach, J.L. Nelssen, R.D. Goodband, S.S. Dritz, J.C. Woodworth, and B.W. James. 2002. Comparison of spray-dried blood meal and blood cells in diets for nursery pigs. J Anim Sci 80:2879-2886.

D. Torralardona, M.R. Conde, I. Badiola, J. Polo, and J. Brufau. 2003. Effect of fishmeal replacement with spray-dried animal plasma and colistin on intestinal structure, intestinal microbiology, and performance of weanling pigs challenged with *Escherichia coli* K99. J Anim Sci 81:1220-1226.

Owusu-Asiedu, C.M. Nyachoti, and R.R. Marquardt. 2003. Response of early-weaned pigs to an enterotoxigenic *Escherichia coli* (K88) challenge when fed diets containing spray-dried porcine plasma or pea protein isolate plus egg yolk antibody, zinc oxide, fumaric acid, or antibiotic. J Anim Sci 81:1790-1798.

Owusu-Asiedu, C.M. Nyachoti, and R.R. Marquardt. 2003. Response of early-weaned pigs to an enterotoxigenic *Escherichia coli* (K88) challenge when fed diets containing spray-dried porcine plasma or pea protein isolate plus egg yolk antibody. J Anim Sci 81:1781-1789.

J.M. DeRouchey, M.d. Tokach, J.L. Nelssen, R.D. Goodband, S.S. Dritz, J.C. Woodworth, M.J. Webster, and B.W. James. 2003. Effects of blood meal pH and irradiation on nursery pig performance. J Anim Sci 81:1013-1022.

C.E. Zier, R.D. Jones, and M.J. Azain. 2004. Use of pet food-grade poultry by-product meal as an alternate protein source in weanling pig diets. J Anim Sci 82:3049-3057.

J. Polo, J.D. Quigley, L.E. Russell, J.M. Campbell, J. Pujols, and P.D. Lukert. 2005. Efficacy of spray-drying to reduce infectivity of pseudorabies and porcine reproductive and respiratory syndrome (PRRS) viruses and seroconversion in pigs fed diets containing spray-dried animal plasma. J Anim Sci 83:1933-1938.

M. Nofrarías, E.G. Manzanilla, J. Pujols, X. Gibert, N. Majó, J. Segalés, and J. Gasa. 2006. Effects of spray-dried porcine plasma and plant extracts on intestinal morphology and on leukocyte cell subsets of weaned pigs. J Anim Sci 84:2735-2742.

M.E. Merchant, et al. 2006. Comparisons of innate immune activity of all known living crocodylian species. Comparative Biochemistry and Physiology, Part B 143:133-137.

Mark Merchant and Adam Britton. 2006. Characterization of serum complement activity of saltwater (*Crocodylus porosus*) and freshwater (*Crocodylus johnstoni*) crocodiles. Comparative Biochemistry and Physiology, Part A 143:488-493.

J.T. Compton, M.E. Merchant, and F.M. Lemieux. Mar. 10, 2006. The effects of American alligator (*Alligator mississippiensis*) serum on growth performance of weaning pigs.

* cited by examiner

BLOOD PRODUCT FROM CROCODYLIAN SPECIES AS A FEED SUPPLEMENT FOR WEANLING PIGS AND POULTRY HATCHLINGS

FIELD OF THE INVENTION

The present invention relates to a feed supplement for weanling pigs and poultry hatchlings consisting of a blood product from at least one Crocodylian species and to a method of increasing weight gain and feed intake of weanling pigs and poultry hatchlings by supplementing their diets with a blood product from at least one Crocodylian species.

BACKGROUND OF THE INVENTION

The age newborn pigs are weaned from the sow can vary depending on the production goals and health status of the farm. The standard weaning age in the swine industry is from 14 to 21 days of age as this maximizes production of the sow, which is placed back in the breeding cycle thereby increasing the number of pigs born by the sow per year. Weaning at this age also provides the weanling pig with positive nutrition and fairly optimal health. If the farm has a poor health status, pigs may be weaned earlier, e.g., from 5 to 7 days of age, and moved to an offsite facility having a higher health status to break the disease cycle of the farm.

Weaning at 14 to 21 days of age or earlier has drawbacks. The digestive system of young pigs is designed to accept and absorb nutrients from milk. Feeding milk to newborn pigs is cost prohibitive. Grain and forage feed products suitable for older pigs are problematic for young pigs because their digestive tracts are not capable of efficiently digesting the feed. Digestion difficulties lead to post-weaning lag, a term used to describe the event when young pigs exhibit slow weight gain and low feed intake.

Efforts have been made to develop more tolerable feed products for young pigs. These "starter" diets are high in digestible nutrients. Such diets consist of processed grains (corn, wheat barley, rice, etc.), gelatinized starches, milk products (dried skim milk, dried whey, lactose, dried whey protein concentrate, casein, etc.), sugars (dextrose, glucose, sucrose), fats and oils (lard, grease, vegetable oils, coconut oil, etc.), animal proteins (fish meal, animal blood meal, meat meal, etc.), and refined, extruded soybeans (soy protein isolate, soy protein concentrate). Even with the use of such starter diets, post-weaning lag remains a concern.

To alleviate post-weaning lag, starter diets for newly-weaned pigs have been supplemented with dried animal plasma. Spray-dried porcine plasma has been used as a feed supplement to increase the weight gain of early-weaned pigs. (Coffey, R. D. et al, 1995. The impact of environmental and antimicrobial agents on the growth response of early-weaned pigs to spray-dried porcine plasma, J. Anim. Sci., 73, 2532-2539, incorporated herein by reference). Weight gain increase in early-weaned pigs fed with a supplement of spray-dried bovine, porcine, or avian blood meal has been found. (Kats, L. J. et al, 1994. The effects of spray-dried blood meal on growth performance of early-weaned pig, J. Anim. Sci., 72, 2860-2869, incorporated herein by reference).

U.S. Pat. No. 5,575,999 discloses a blended powdered feed supplement comprising animal plasma (e.g., pig or cow plasma) and a microbial fermentation product, primarily amylase.

U.S. Pat. No. 5,785,990 discloses a liquid feed fortifier for preruminant, bovine calves comprising animal plasma and other ingredients (e.g., vitamins, minerals, electrolytes, etc.).

U.S. Pat. No. 6,004,576 discloses a feed supplement of granulated animal plasma (e.g., porcine, bovine, ovine, equine, or avian plasma).

U.S. Pat. No. 6,569,447 discloses a performance-enhancing feed supplement comprising spray-dried porcine plasma and spray-dried hyperimmune egg.

Even with the use of starter diets supplemented with animal plasma, the practice of supplementing feed with subtherapeutic doses of antibiotics to improve feed efficiency and growth is routine. The specific mode of action for enhanced growth is unknown; the improvement in efficiency is due to a more favorable gut microflora.

Subtherapeutic use of antibiotics in diets of farm production animals was first introduced in 1946 when the addition of subtherapeutic levels of antimicrobials was found to enhance growth in poultry. (Moore, P. R., et al., 1946. Use of sulfasuxidine, steptothricin, and streptomycin in nutritional studies with the chick, J. Biol. Chem., 165:437-445, incorporated by reference herein). Today, antimicrobial agents are incorporated in approximately 90% of weanling, 75% grower, and 50% of finishing swine diets. As mentioned above, pigs are typically weaned early (on average at 21 days of age). Because weaning pigs receive immunity through the dam's colostrum, weaning interrupts this process. With an immature immune system, early-weaned pigs are not able to effectively combat bacterial disease until about four months of age. Their diets are usually fortified with antibiotics to prevent disease but also to increase growth and feed efficiency.

Given the widespread subtherapeutic use of antibiotics, consumers of animal products are becoming concerned with the potential for bacterial resistance. The European Union has banned the use of subtherapeutic antibiotics in swine feed. Major food service companies in Europe have gone so far as to develop policies regulating the use of antibiotics in animals they purchase. Consumers and the food service industry in the United States have signaled a desire to move in the same direction. As a result, researchers are striving to find alternatives to antibiotics such as probiotics, competitive exclusion, enzymes, immune modulators, organic acids, minerals, vitamins, conjugated linoleic acids, phospholipids, amino acids, carnitine, carbohydrates, and herbs. (Doyle, E., 2002. Alternative to antibiotic use for growth promotion in animal husbandry; A Review of Scientific Literature, Report NPPC, 98, 162, incorporated herein by reference).

Despite the development of diets supplemented with animal plasma and of alternatives to the subtherapeutic use of antibiotics, the need still exists for feed supplements that increase weight gain, feed intake, and promote gut health so that the use of subtherapeutic antibiotics can be reduced or eliminated.

SUMMARY OF INVENTION

It is an object of the present invention to provide a novel feed supplement, feed composition, and method that increases weight gain in weanling pigs and poultry hatchlings.

It is another object of the present invention to provide a novel feed supplement, feed composition, and method that increases feed intake in weanling pigs and poultry hatchlings.

It is another object of the present invention to provide a novel feed supplement, feed composition, and method that is expected to promote gut health in weanling pigs and poultry hatchlings.

It is another object of the present invention to provide a novel feed supplement, feed composition, and method that is expected to decrease incidences of gut related diseases and bacterial infections in weanling pigs and poultry hatchlings.

It is another object of the present invention to provide a novel feed supplement, feed composition, and method that is expected to reduce or eliminate subtherapeutic use of antibiotics in feed for weanling pigs and poultry hatchlings.

These and other objects of the present invention are achieved by a novel feed supplement for weanling pigs or poultry hatchlings that comprises a blood product from one or more members of the Crocodylia or more preferably from at least one Crocodylian species. The feed supplement is fed to weanling pigs or poultry hatchlings in an amount effective to increase their weight gain and/or feed intake. The feed supplement is also expected to promote gut health. Promoting gut health includes reducing the likelihood of gut related diseases or bacterial infections. The blood product may be whole blood, hemolyzed blood, serum, or plasma in liquid or solid form. In solid form, the blood product may be a spray-dried, lyophilized, or granular solid.

In another embodiment of the present invention a novel feed composition for weanling pigs or poultry hatchlings is provided. The feed composition contains a feed supplement and a high nutrient feed such as a starter diet. The feed supplement consists of a blood product from one or more members of the Crocodylia or more preferably from at least one Crocodylian species. The blood product may be whole blood, hemolyzed blood, serum, or plasma. The whole blood, hemolyzed blood, serum, or plasma may be a liquid or solid (e.g., a spray-dried, lyophilized, or granular solid).

The feed composition may be fed to weanling pigs or poultry hatchlings in an amount effective to increase their weight gain and/or feed intake. It is also expected to promote gut health. The feed composition preferably contains 0.1% or more by weight of the feed supplement. This amount has been found effective to increase weight gain and feed intake in weanling pigs and poultry hatchlings. The feed composition may also contain 0.1% to 5.0% by weight of feed supplement, and more preferably, 0.5% by weight of feed supplement.

The present invention also is a method of increasing weight gain and/or feed intake of weanling pigs or poultry hatchlings. The method is also expected to promote gut health of weanling pigs and poultry hatchlings. The method includes feeding the weanling pigs or poultry hatchlings a feed supplement. The feed supplement consists of or includes a blood product from one or more members of the Crocodylia or more preferably from at least one Crocodylian species. The feed supplement is fed to the pigs or hatchlings in an amount effective to increase their weight gain and/or feed intake. It is also expected to promote their gut health. The blood product may be whole blood, hemolyzed blood, serum, or plasma in liquid or solid form. In solid form, the blood product may be a spray-dried, lyophilized, or granular solid.

The method of the present invention may include combining or mixing the feed supplement with a high nutrient feed (e.g., starter diet) to form a feed composition. The feed composition may contain 0.1% or more by weight of feed supplement. The feed composition may also contain 0.1% to 5.0% by weight of feed supplement. Preferably, the feed composition contains 0.5% by weight of feed supplement.

It is to be understood that weaned pigs and poultry hatchlings that have not reached the age of maturity may have their diets supplemented with a blood product from at least one Crocodylian species, e.g., whole blood, hemolyzed blood, serum, or plasma. Preferably, pigs should be weaned sometime between the ages of 14 to 21 days and diet supplementation started immediately or within 24 hours of weaning. For broiler chicks, it is preferred to start diet supplementation immediately after hatching. The weaned pigs and poultry hatchlings may be fed with the feed supplement ad libitum. The amount of diet supplementation with a blood product from at least one Crocodylian species may be decreased as the weaned pig or poultry hatchling gains weight.

The blood product (e.g., whole blood, hemolyzed blood, serum, or plasma) constituting the feed supplement of the present invention may be from one or more of the following members of the Crocodylia:

Alligatoriodea:
Alligator mississippiensis
Alligator sinensis
Caiman crocodilus
Caiman latirostris
Caiman yacare
Melanosuchus niger
Paleosuchus palpebrosus
Paleosuchus trigonatus
Crocodyliodea:
Crocodylus acutus
Crocodylus cataphractus
Crocodylus intermedius
Crocodylusjohnsoni
Crocodylus mindorensis
Crocodylus moreletti
Crocodylus niloticus
Crocodylus novaeguineae
Crocodylus palustris
Crocodylus porosus
Crocodylus rhombifer
Crocodylus siamensis
Osteolaemus tetraspis
Gavialoidea:
Gavialis gangeticus
Tomistoma schlegelii The feed supplement of the present invention may comprise a blood product from any one of the Crocodylian species listed above or a combination of blood products from two or more of the aforesaid Crocodylian species. Preferably, the feed supplement comprises a blood product from the American alligator (*Alligator mississippiensis*). More preferably, the feed supplement comprises whole blood, hemolyzed blood, serum, or plasma from the American alligator (*Alligator mississippiensis*) in liquid or solid form (e.g., a spray-dried, lyophilized, or granular solid).

DETAILED DESCRIPTION OF PREFERRED EMBODIMENT

The present invention is a feed supplement for weanling pigs and poultry hatchlings. Poultry hatchlings include the young of domestic fowl, including chickens, turkeys, ducks, and geese.

The feed supplement of the present invention contains blood or a blood product from one or more members of the Crocodylia. For example, the blood product may be obtained from one or more of the following Crocodylian species: *Alligator mississippiensis; Alligator sinensis; Caiman*

*crocodilus; Caiman latirostris; Caiman yacare; Melanosuchus niger; Paleosuchus palpebrosus; Paleosuchus trigonatus; Crocodylus acutus; Crocodylus cataphractus; Crocodylus intermedius; Crocodylus johnsoni; Crocodylus mindorensis; Crocodylus moreletti; Crocodylus niloticus; Crocodylus novaeguineae; Crocodylus palustris; Crocodylus porosus; Crocodylus rhombifer; Crocodylus siamensis; Osteolaemus tetraspis; Gavialis gangeticus*; or *Tomistoma schlegelii*. It is preferred that the feed supplement of the present invention contain blood or a blood product from the American alligator (*Alligator mississippiensis*).

The foregoing describes the collection and processing of blood from the American alligator. It is, however, to be understood that such collection and processing procedures are equally applicable to any other member of the Crocodylia.

The American alligator's natural habitat is primarily in the southeastern part of the United States, including the States of Florida, Louisiana, and Texas. The alligator is traditionally hunted or farmed for its skin and meat. During the harvesting process, the alligator's blood is customarily discarded. The present invention involves the collection and use of the alligator's blood. The present invention, therefore, seeks to maximize and make efficient use of alligator by-products during the harvesting process.

When the alligator is harvested for its skin and meat, the present invention collects and stores the alligator's blood. Typically during the harvesting process, the alligator is drained of its blood. For purposes of collection, the blood may be drained and deposited into a funnel which leads to a collecting tank. The blood may be stored in the collecting tank. Blood from more than one alligator may be pooled in the collecting tank. The collecting tank may be any tank made of non-corrosive material such as plastic or stainless steel. Anti-coagulating agents may be added to the blood to prevent clotting. Such anti-coagulating agents may include ethylenediamine tetraacetate (EDTA), citrate, or heparin. The amount of anti-coagulating agent required to prevent clotting is within the skill of the ordinary artisan to which the present invention is directed.

The present invention also may involve the collection of blood from live alligators either captured in the wild or raised on alligator farms. In this embodiment of the present invention, the alligator is not sacrificed but becomes a blood donor. On a periodic basis, blood is collected from the alligator in an amount that does not harm the animal. The alligator then regenerates the blood lost during the collection process by inherent biological functions. After a certain period of time sufficient for the alligator to regenerate the blood lost during the collection process, blood is collected again. This process may continue until such time that a decision is made to stop collecting blood from the particular alligator or the alligator dies. The amount of blood collected from the alligator at any one time and the period of time necessary for the alligator to regenerate blood after collection are well within the skill of an ordinary artisan to which to invention is directed.

In a preferred embodiment of the present invention, blood from an alligator is obtained from the alligator's spinal vein aseptically using a 60 cc syringe and an 18 ga. needle. The blood may then be transferred to a container made of a non-corrosive material such as plastic or stainless steel. Blood collected from more than one alligator may be pooled in the container. To prevent clotting, an anti-coagulating agent may be added to the blood. Such anti-coagulating agents may include ethylenediamine tetraacetate (EDTA), citrate, or heparin. The amount of anti-coagulating agent required to prevent clotting is within the skill of the ordinary artisan to which the present invention is directed.

In an embodiment of the present invention, whole blood from the alligator is used as a feed supplement for weanling pigs (e.g., early-weaned starter pigs) and poultry hatchlings. Alternatively, hemolyzed blood, serum, or plasma prepared from the blood of the alligator may be used as a feed supplement. The feed supplement is fed to weanling pigs or poultry hatchlings in an amount effective to increase their weight gain and/or feed intake, and is also expected to promote or enhance their gut health to reduce incidences of gut related diseases or bacterial infections. The weanling pigs or poultry hatchlings may be fed the feed supplement in specified portions or fed ad libitum. The amount of feed supplement fed to a weanling pig or poultry hatchling may vary depending on the age, weight, size, or health of the pig or hatchling. Preferably, the feed supplement makes up 0.1% or more by weight of the diet of the pig or hatchling, or more preferably 0.1% to 5.0% by weight of the diet, or even more preferably 0.5% by weight of the diet.

Alligator serum is the clear, amber, slightly alkaline fluid of the blood from which cellular elements and fibrinogen have been removed by clotting. To prepare the serum for use as a feed supplement, whole blood collected from the alligator is allowed to clot at ambient temperature for approximately 3 hours. The clotted whole blood is then centrifuged at least at 5,000×g for at least 10 minutes or more preferably at 12,000×g for 30 minutes to subject the clotted blood to a high centrifugal force which increases serum yield. The serum is then collected and stored in a suitable container for later use as a feed supplement.

Alligator plasma is the liquid part of the blood that contains plasma proteins, fibrinogen, and dissolved carbohydrates such as glucose. To obtain the plasma, alligator whole blood is centrifuged at least at 1,000×g for at least 5 minutes or more preferably at 2,000×g for 15 minutes. After centrifuging, the suspended red blood cells, leukocytes, and platelets are separated from the plasma liquid. The plasma is stored in a suitable container for later use as a feed supplement.

Hemolyzed blood has undergone hemolysis in which the red blood cells are ruptured to release cellular contents such as hemoglobin. Hemolysis or the dissolution of the red blood cells may be caused by chemicals, heating, freezing, or biological agents. In the preferred embodiment of the present invention, the hemolyzed blood is produced by adding at least 1.5 volumes of distilled water to 1 volume of anti-coagulated alligator whole blood. This will cause the red bloods in the alligator whole blood to lyse. The hemolyzed alligator blood is stored in a suitable container for later use as a feed supplement.

The feed supplement containing alligator whole blood, hemolyzed blood, serum, or plasma may be a liquid or a solid. Spray-dried, lyophilized, or granular solids are examples of the solid form. The production of a spray-dried or granular alligator blood product may be accomplished by methods well known in the art to which the present invention pertains. For example, U.S. Pat. No. 6,004,576 (which is incorporated herein by reference) describes techniques for producing a spray-dried and granular blood product. Hemolyzed blood, serum, or plasma in lyophilized form may be prepared by rapid freezing and dehydration of the biological substance. It may be made ready for use as a supplement by adding sterile distilled water. Techniques for lyophilization are well known in the art to which the present invention pertains.

The feed supplement consisting of or containing alligator whole blood, hemolyzed blood, serum or plasma may be fed to weanling pigs or poultry hatchlings directly or it may be combined or mixed with the diet or feed customarily fed to such pigs and poultry hatchlings, as for example, a high nutrient starter diet.

When combining or mixing the feed supplement with a starter diet, it is preferred to include the feed supplement in a weight ratio of 0.1% or more by weight of the total weight of the feed composition. More preferably, the amount of feed supplement in the feed composition should be 0.1% to 5.0% by weight of the total weight of the feed composition. It also been found that 0.5% by weight of feed supplement to the total weight of the feed composition is most preferred to optimize and increase weight gain and feed intake and is also expected to promote or enhance the gut health of the pig or hatchling.

In a preferred embodiment of the present invention, a weaned starter pig is fed the feed supplement or feed composition as soon as the animal is weaned or within 24 hours of weaning. Preferably, the pig is weaned within 14 to 21 days of its birth and fed the feed supplement or feed composition immediately upon such weaning or within 24 hours. The pig preferably is fed the feed supplement or feed composition until the animal reaches the age of 28 to 35 days. It is to be understood that supplementation of the weaned pig's diet may begin at anytime after weaning (preferably sometime before the pig reaches the age of 28 to 35 days) and may be terminated anytime after the pig reaches the age of 28 to 35 days.

The start of supplementation of the weaned pigs' diet using until the blood product of the present invention depends on a variety of factors such as the pig's weight, health, and feed intake. The start of such supplementation may begin at any time after weaning when the factors indicate that supplementation is necessary to obtain optimum growth and health. Starting supplementation at weaning between 14 and 21 days of birth is preferred but not required if the young pig is gaining sufficient weight. Post-weaning lag could exhibit later in certain weaned pigs so that the start of supplementation could begin anywhere from 1 to 21 days after weaning or at the onset of post-weaning lag. Supplementation preferably continues for 21 days but it may be terminated earlier or continued longer depending upon whether the young pig has achieved sufficient or optimum growth.

As the weaned pig develops and its weight increases, the amount of feed supplement fed to the pig may be reduced. For example, the pig may be fed a feed composition containing 0.5% by weight feed supplement from weaning through post-weaning day 12. If the pig has increased its weight sufficiently at post-weaning day 12, the pig may be fed a feed composition containing 0.1% by weight feed supplement from post-weaning day 12 through post-weaning day 21.

Poultry hatchlings may be fed the feed supplement or a feed composition immediately upon hatching. The hatchlings should be fed the feed supplement or feed composition for 15 to 25 days and more preferably, for 20 days. The amount of feed supplement or feed composition fed to the hatchlings may depend on their weight gain and feed intake. If the hatchlings show optimum weight gain, the amount of supplementation may be reduced. For example, a hatchling may be fed a feed composition containing 0.5% by weight feed supplement from hatching through day 10. If the hatchling has increased its weight sufficiently at day 10, the hatchling may be fed a feed composition containing 0.1% by weight feed supplement from day 111 through day 25.

The effectiveness of the feed supplement of the present invention to increase weight gain and/or feed intake in weanling pigs and poultry hatchlings is demonstrated in the following examples.

EXAMPLE 1

Six weanling pigs with an average initial body weight of 5.90 kg and an average initial age of 24 days were allotted to a randomized block design consisting of 2 treatments. Experimental units were represented by 1.1×1.7 m pens containing 3 pigs per pen with 1 replication per treatment. Pigs were contained in an environmentally controlled nursery with an average temperature of 29.44° C. Pigs were given ad libitum access to water and feed.

Diets consisted of a complex nursery basal feed (B) with 0.75% by weight antibiotic and a mixture of complex nursery basal feed without antibiotic supplemented with 0.5% by weight American alligator serum (BS) (Table 1(a)). The diets were fed from day 0-21 but all pigs were switched to B diet on day 14. Pen weights and feed intakes were collected on day 0, 7, 13 and 21. Table 1(b) shows the average daily gain (ADG), average daily feed intake (ADFI), and a gain:feed ratio.

TABLE 1(a)

Composition of Experimental Diets Fed to Weanling Pigs (as fed, %)

| Ingredient | Phase 1 | | Phase 2 | |
|---|---|---|---|---|
| | Basal | Serum | Basal | Serum |
| Corn | 36.94 | 36.94 | 46.96 | 46.96 |
| Soybean meal (48.5% CP) | 24.52 | 24.52 | 31.44 | 31.44 |
| Whey | 15.00 | 15.00 | 10.00 | 10.00 |
| Lactose | 5.00 | 5.00 | — | — |
| AP 920 | 5.00 | 5.00 | — | — |
| Fishmeal, menhaden | 6.00 | 6.00 | 5.00 | 5.00 |
| Dry fat | 4.00 | 4.00 | 3.00 | 3.00 |
| Monocalcium phosphate | 0.68 | 0.82 | 0.57 | 0.57 |
| Limestone | 0.72 | 0.72 | 0.68 | 0.68 |
| Trace Minerals[1] | 0.10 | 0.10 | 0.10 | 0.10 |
| ZMC-Fe[2] | 0.10 | 0.10 | 0.10 | 0.10 |
| Se premix[3] | 0.05 | 0.05 | 0.05 | 0.05 |
| Salt | 0.25 | 0.25 | 0.50 | 0.50 |
| Zinc oxide | 0.28 | 0.28 | 0.28 | 0.28 |
| Vitamins[4] | 0.50 | 0.50 | 0.50 | 0.50 |
| L-Lysine HCl | — | — | — | — |
| DL-Methionine | 0.07 | 0.07 | 0.02 | 0.02 |
| Choline chloride | 0.05 | 0.05 | 0.05 | 0.05 |
| Sodium bentonite | 0.50 | 0.50 | 0.50 | 0.50 |
| Antibiotic[5] | 0.75 | — | 0.75 | — |
| Flavor | 0.08 | 0.08 | 0.08 | 0.08 |
| Calculated composition: | | | | |
| Crude protein | 24.14 | 24.14 | 23.10 | 23.10 |
| Lysine | 1.60 | 1.60 | 1.40 | 1.40 |
| Tryptophan | 0.32 | 0.32 | 0.28 | 0.28 |
| Threonine | 1.06 | 1.06 | 0.92 | 0.92 |
| Met + Cys | 0.92 | 0.92 | 0.79 | 0.79 |
| Calcium | 0.90 | 0.90 | 0.80 | 0.90 |
| Phosphorus | 0.79 | 0.79 | 0.69 | 0.69 |

[1]Provided the following per kilogram of diet: Zn (zinc sulfate), 127; Fe (ferrous sulfate monohydrate), 127; Mn (manganous sulfate), 20; Cu (copper sulfate), 12.7; 1 (calcium iodate), .80 mg.
[2]Provided the following per kilogram of diet: Zn, 40 mg; Mn, 7.5 mg; Cu, 6 mg; Fe, 25 mg.
[3]Provided .3 mg Se per kilogram of diet.
[4]Provided the following per kilogram of diet: vitamin A, 11,023 IU; vitamin D, 3,307 IU; vitamin E, 88 IU; menadione (menadionine pyrimidinol bisulfite), 8.3 mg; riboflavin, 13 mg; pantothenic acid, 50 mg; niacin, 88 mg; vitamin $B_{12}$, 61 μg; biotin, 441 μg; choline (as choline chloride), 882 mg; folic acid, 3.3 mg, pyridoxine, 4.41; thiamin, 4.41; and vitamin C, 110 μg.
[5]Neo TM 10/10 - Neo-Terramycin ® (Neomycin Oxytetracycline), Active drug: Oxtetracycline and Neomycin Sulfate.

TABLE 1(b)

Effect of 0.5% Serum on Growth Performance of Weanling Pigs

| Item | Basal (B) | A. Serum (BS) | SEM[1] |
|---|---|---|---|
| Day 0-7 | | | |
| ADG, g | 86.48 | 259.4 | 46.37 |
| ADFI, g | 151 | 216.2 | 32.43 |
| Gain:Feed | 573 | 1200 | 313.5 |
| Day 7-13 | | | |
| ADG, g | 403.6 | 479.2 | 23.23 |
| ADFI, g | 454 | 757 | 75.7 |
| Gain:Feed | 889 | 633 | 48.5 |
| Day 13-21 | | | |
| ADG, g | 340.5 | 529.7 | 82.46 |
| AFI, g | 454 | 757 | 151.3 |
| Gain:Feed | 750 | 700 | 25.0 |
| Day 0-21 | | | |
| ADG, g | 273 | 425.2 | 50.06 |
| AFI, g | 353 | 540 | 93.7 |
| Gain:Feed | 776 | 787 | 5.5 |

[1]Standard error of mean

The results demonstrate that pigs fed a basal diet without antibiotic but supplemented with 0.5% by weight American alligator serum performed better than pigs fed a basal diet containing an antibiotic. For instance, over a 21 day period, pigs fed a basal diet without antibiotic but supplemented with 0.5% by weight alligator serum had an average daily weight gain that was 152.2 g more than the average daily weight gain of pigs fed a basal diet containing 0.75% by weight antibiotic. The average daily feed intake for pigs fed a basal diet without antibiotic but supplemented with 0.5% by weight alligator serum was 187 g more than the average daily feed intake of pigs fed a basal diet containing 0.75% by weight antibiotic.

EXAMPLE 2

100 weanling pigs with an average initial body weight of 7.44 kg and an average initial age of 24 days were allotted to a randomized block design consisting of 4 treatments. Experimental units were represented by 1.1×1.7 m pens containing 3, 4, or 5 pigs per pen with 6 replications per treatment. Pigs were contained in an environmentally controlled nursery with an average temperature of 29.44° C. Pigs were given ad libitum access to water and feed.

Diets consisted of a complex nursery basal feed without antibiotic (B), a mixture of complex nursery basal feed with 0.75% by weight antibiotic (BA), a mixture of complex nursery basal feed without antibiotic supplemented with 0.5% by weight American alligator serum (BS), and a mixture of complex nursery basal feed with 0.75% by weight antibiotic and 0.5% by weight American alligator serum (BAS) (Table 1(a)). The diets were fed from day 0-21. Pen weights and feed intakes were collected on day 0, 7, 14, and 21. Table 2 shows the average daily gain (ADG), average daily feed intake (ADFI), and a gain:feed ratio.

TABLE 2

Effect of 0.5% Serum on Growth Performance of Weanling Pigs

| Item | B | BA | BS | BAS | SEM[1] |
|---|---|---|---|---|---|
| Day 0-7 | | | | | |
| ADG, g | 454.8 | 477.3 | 496.3 | 446.5 | 14.69 |
| ADFI, g | 457.5 | 466.8 | 493.9 | 452.7 | 26.76 |
| Gain:Feed | 0.994 | 1.02 | 1.00 | 0.986 | 0.007 |
| Day 7-14 | | | | | |
| ADG, g | 495.2 | 547.9 | 494.5 | 519.1 | 9.82 |
| ADFI, g | 755.3 | 814.6 | 785.2 | 779.4 | 21.73 |
| Gain:Feed | 0.656 | 0.673 | 0.630 | 0.666 | 0.009 |
| Day 0-14 | | | | | |
| ADG, g | 475.0 | 512.6 | 495.4 | 482.8 | 9.45 |
| ADFI, g | 590.2 | 624.4 | 639.6 | 616.0 | 25.38 |
| Gain:Feed | 0.805 | 0.821 | 0.775 | 0.784 | 0.01 |
| Day 14-21 | | | | | |
| ADG, g | 541.6 | 619.6 | 604.5 | 700.9 | 18.2 |
| ADFI, g | 980.64 | 1098.68 | 1080.95 | 1206.78 | 38.95 |
| Gain:Feed | 0.552 | 0.564 | 0.559 | 0.581 | 0.006 |
| Day 0-21 | | | | | |
| ADG, g | 504.7 | 584.1 | 561.8 | 580.0 | 12.1 |
| ADFI, g | 787.51 | 873.70 | 850.06 | 876.64 | 25.65 |
| Gain:Feed | 0.641 | 0.669 | 0.661 | 0.662 | 0.006 |

[1]Standard error of mean

The results demonstrate that pigs fed with basal diets without antibiotic but supplemented with 0.5% by weight American alligator serum performed better than pigs fed a basal diet without antibiotic and pigs fed a basal diet with antibiotic. For instance, over a 21 day period, pigs fed basal diets without antibiotic but supplemented with 0.5% by weight alligator serum had an average daily weight gain that was 57.10 g more than the average daily weight gain of pigs fed a basal diet without antibiotic. The average daily feed intake for pigs fed basal diets without antibiotic but supplemented with 0.5% by weight alligator serum was 62.55 g more than the average daily feed intake of pigs fed a basal diet without antibiotic. The average daily feed intake for pigs fed a basal diet containing 0.75% by weight antibiotic supplemented with 0.5% by weight alligator serum was 2.94 g more than the average daily feed intake of pigs fed a basal diet containing 0.75% by weight antibiotic.

EXAMPLE 3

124 broiler chicks with an average initial body weight of 45.04 g and an age of one day were allotted to a randomized design consisting of 4 treatments. Experimental units were represented by 33×99 cm pens containing 6 or 7 broilers per coop with 5 replications per treatment. Broilers were contained in an environmentally controlled nursery with an average temperature of 35° C. Broilers were given ad libitum access to water and feed.

Diets consisted of a basal feed (B), a mixture of basal feed and litter (BL), a mixture of basal feed supplemented with 0.5% by weight American alligator serum (BS), and a mixture of basal feed and litter supplemented with 0.5% by weight American alligator serum (BLS) (Table 3(a)). The diets were fed from day 0-19. Two birds were removed due to slow growth and data was adjusted accordingly. The broilers were fed for 5 additional days after completion of the trial. Chick weights and feed intakes were collected on day 0, 7, 14, and 19. Table 3(b) shows the average daily gain (ADG), average daily feed intake (ADFI), and a gain:feed ratio.

TABLE 3(a)

Composition of Experimental Diets Fed to Broiler Chicks (as fed, %)

| Ingredient | Basal | +Litter |
|---|---|---|
| Corn | 45.28 | 45.28 |
| Soybean meal (47.5% CP) | 37.82 | 37.82 |
| Oil | 7.74 | 7.74 |
| Monocalcium phosphate | 1.54 | 1.54 |
| Limestone | 1.47 | 1.47 |
| Trace minerals[1] | 0.25 | 0.25 |
| Salt | 0.50 | 0.50 |
| Vitamins[2] | 0.05 | 0.05 |
| L-threonine | 0.09 | 0.09 |
| DL-Methionine | 0.21 | 0.21 |
| Choline chloride | 0.05 | 0.05 |
| Litter | — | 0.05 |
| Cellulose | 0.05 | — |
| Calculated composition: | | |
| ME, kcal/kg | 3,200 | 3,200 |
| Crude protein | 22.00 | 22.00 |
| Lysine | 1.26 | 1.26 |
| Tryptophan | 0.27 | 0.27 |
| Threonine | 0.92 | 0.92 |
| Met + Cys | 0.91 | 0.91 |
| Calcium | 1.00 | 1.00 |
| Phosphorus | 0.71 | 0.71 |

[1]Provides the following per kilogram of diet: copper (cupric sulfate pentahydrate), 7.00 mg; iodine (calcium iodate), 1.00 mg; iron (ferrous sulfate monohydrate), 50.00 mg; manganese (manganese sulfate monohydrate), 100.00 mg; selenium (sodium selenite), 0.15 mg; and zinc (zinc sulfate monohydrate), 75 mg.
[2]Provides the following per kilogram of diet: vitamin A, 8,000 IU; vitamin $D_3$, 3,000 IU; vitamin E, 25 IU; menadione, 1.5 mg; riboflavin, 10 mg; and thiamin, 3 mg.

TABLE 3(B)

Effect of 0.5% Serum on Growth Performance of Broilers

| Item | B | BL | BS | BLS | SEM[1] |
|---|---|---|---|---|---|
| Day 0-7 | | | | | |
| ADG, g | 15.8 | 14.2 | 16.4 | 16.9 | 0.38 |
| ADFI, g | 17.3 | 20.4 | 16.9 | 17.9 | 0.83 |
| Gain:Feed | 0.913 | 0.696 | 0.970 | 0.944 | 0.06 |
| Day 7-14 | | | | | |
| ADG, g | 37.0 | 38.1 | 35.8 | 35.4 | 1.07 |
| ADFI, g | 46.5 | 49.2 | 46.0 | 47.6 | 1.41 |
| Gain:Feed | 0.796 | 0.774 | 0.778 | 0.744 | 0.01 |
| Day 0-14 | | | | | |
| ADG, g | 26.39 | 26.14 | 26.10 | 26.18 | 0.57 |
| ADFI, g | 31.87 | 34.81 | 31.44 | 32.72 | 0.89 |
| Gain:Feed | 0.828 | 0.751 | 0.830 | 0.800 | 0.02 |
| Day 14-19 | | | | | |
| ADG, g | 43.38 | 43.69 | 44.54 | 46.39 | 0.68 |
| ADFI, g | 74.33 | 73.88 | 72.64 | 77.14 | 4.22 |
| Gain:Feed | 0.580 | 0.590 | 0.610 | 0.600 | 0.01 |
| Day 0-19 | | | | | |
| ADG, g | 31.01 | 32.09 | 31.58 | 32.55 | 0.33 |
| ADFI, g | 38.04 | 40.78 | 37.83 | 39.38 | 1.57 |
| Gain:Feed | 0.820 | 0.790 | 0.830 | 0.830 | 0.01 |

[1]Standard error of mean

The results demonstrate that broiler chicks fed a basal diet supplemented with 0.5% by weight American alligator serum performed better than broiler chicks fed a basal diet. For instance, over a 19 day period, broiler chicks fed a basal diet supplemented with 0.5% by weight American alligator serum had an average daily weight gain that was 0.57 g more than the average daily weight gain of broiler chicks fed a basal diet. Broiler chicks fed a basal diet with litter supplemented with 0.5% by weight American alligator serum had an average daily weight gain that was 0.46 g more than the average daily weight gain of broiler chicks fed a basal diet with litter.

EXAMPLE 4

124 broiler chicks with an average initial body weight of 42.37 g and an age of one day were allotted to a randomized design consisting of 4 treatments. Experimental units were represented by 33×99 cm pens containing 6 or 7 broilers per coop with 5 replications per treatment. Broilers were contained in an environmentally controlled nursery with an average temperature of 35° C. Broilers were given ad libitum access to water and feed.

Diets consisted of a basal feed (B), a mixture of basal feed and litter (BL), a mixture of basal feed supplemented with 0.5% by weight American alligator serum (BS), and a mixture of basal feed and litter supplemented with 0.5% by weight American alligator serum (BLS) (Table 3(a)). The diets were fed from day 0-15. Chick weights and feed intakes were collected on day 0, 3, 6, 9, 12, and 15. Table 4 shows the average daily gain (ADG), average daily feed intake (ADFI), and a gain:feed ratio.

TABLE 4

Effect of 0.5% Serum on Growth Performance of Broilers

| Item | B | BL | BS | BLS | SEM[1] |
|---|---|---|---|---|---|
| Day 0-3 | | | | | |
| ADG, g | 8.6 | 10.4 | 8.7 | 9.9 | 0.23 |
| ADFI, g | 9.7 | 11.24 | 9.8 | 11.24 | 0.51 |
| Gain:Feed | 0.887 | 0.925 | 0.888 | 0.881 | 0.01 |
| Day 3-6 | | | | | |
| ADG, g | 17.3 | 16.8 | 17.4 | 17.5 | 0.24 |
| ADFI, g | 16.9 | 16.6 | 17.2 | 16.6 | 0.33 |
| Gain:Feed | 1.02 | 1.01 | 1.01 | 1.05 | 0.009 |
| Day 6-9 | | | | | |
| ADG, g | 21.9 | 14.7 | 21.9 | 23.7 | 0.62 |
| ADFI, g | 32.7 | 28.2 | 31.2 | 32.1 | 0.77 |
| Gain:Feed | 0.669 | 0.521 | 0.702 | 0.738 | 0.05 |
| Day 0-9 | | | | | |
| ADG, g | 15.9 | 14.0 | 16.0 | 17.0 | 0.26 |
| ADFI, g | 20.60 | 19.34 | 20.0 | 20.7 | 0.49 |
| Gain:Feed | 0.771 | 0.724 | 0.80 | 0.821 | 0.02 |
| Day 9-12 | | | | | |
| ADG, g | 27.9 | 25.6 | 26.2 | 27.4 | 0.55 |
| ADFI, g | 31.7 | 26.3 | 30.3 | 30.3 | 0.50 |
| Gain:Feed | 0.880 | 0.973 | 0.865 | 0.904 | 0.02 |
| Day 12-15 | | | | | |
| ADG, g | 31.0 | 29.0 | 28.7 | 34.8 | 0.98 |
| ADFI, g | 38.0 | 37.1 | 40.1 | 43.6 | 1.15 |
| Gain:Feed | 0.816 | 0.782 | 0.716 | 0.798 | 0.02 |
| Day 0-15 | | | | | |
| ADG, g | 21.35 | 19.3 | 20.6 | 22.7 | 0.35 |
| ADFI, g | 25.62 | 23.9 | 25.7 | 26.78 | 0.33 |
| Gain:Feed | 0.833 | 0.808 | 0.802 | 0.848 | 0.01 |

[1]Standard error of mean

The results demonstrate that broiler chicks fed a basal diet supplemented with 0.5% by weight American alligator serum performed better than broiler chicks fed a basal diet. For instance, over a 15 day period, broiler chicks fed a basal diet supplemented with 0.5% by weight American alligator serum had an average daily feed intake that was 0.08 g more than the average daily feed intake of broiler chicks fed a basal diet. Broiler chicks fed a basal diet with litter supplemented with 0.5% by weight American alligator serum had an average daily weight gain that was 3.4 g more than the average daily weight gain of broiler chicks fed a basal diet with litter. Broiler chicks fed a basal diet with litter supplemented with 0.5% by weight American alligator serum had an average daily feed intake that was 2.88 g more than the average daily feed intake of broiler chicks fed a basal diet with litter.

EXAMPLE 5

240 broiler chicks with an average initial body weight of 40.54 g and an age of one day were allotted to a randomized design consisting of 4 treatments. Experimental units were represented by 33×99 cm pens containing 6 or 12 broilers per coop with 8 replications per treatment. Broilers were contained in an environmentally controlled nursery with an average temperature of 35° C. Broilers were given ad libitum access to water and feed.

Diets consisted of a basal feed (B), a mixture of basal feed and litter (BL), a mixture of basal feed supplemented with 0.5% by weight American alligator serum (BS), and a mixture of basal feed and litter supplemented with 0.5% by weight American alligator serum (BLS) (Table 3(a)). The diets were fed from day 0-14. Chick weights and feed intakes were collected on day 0, 4, 7, 11, and 14. Table 5 shows the average daily gain (ADG), average daily feed intake (ADFI), and a gain:feed ratio.

TABLE 5

Effect of 0.5% Serum on Growth Performance of Broilers

| Item | B | BL | BS | BLS | SEM[1] |
|---|---|---|---|---|---|
| Day 0-4 | | | | | |
| ADG, g | 7.1 | 7.5 | 6.5 | 7.8 | 0.44 |
| ADFI, g | 4.1 | 4.41 | 5.04 | 6.43 | 0.44 |
| Gain:Feed | 1.73 | 1.70 | 1.29 | 1.21 | 0.135 |
| Day 4-7 | | | | | |
| ADG, g | 14.9 | 15.7 | 14.7 | 16.2 | 0.49 |
| ADFI, g | 18.41 | 18.92 | 17.32 | 17.57 | 0.70 |
| Gain:Feed | 0.81 | 0.83 | 0.85 | 0.92 | 0.02 |
| Day 0-7 | | | | | |
| ADG, g | 10.5 | 11.1 | 10.1 | 11.6 | 0.41 |
| ADFI, g | 10.34 | 10.62 | 10.45 | 11.21 | 0.49 |
| Gain:Feed | 1.02 | 1.05 | 0.97 | 1.03 | 0.017 |
| Day 7-11 | | | | | |
| ADG, g | 24.9 | 24.4 | 24.6 | 24.4 | 0.54 |
| ADFI, g | 18.8 | 18.11 | 18.94 | 19.01 | 0.68 |
| Gain:Feed | 1.32 | 1.35 | 1.30 | 1.28 | 0.01 |
| Day 0-11 | | | | | |
| ADG, g | 27.9 | 25.6 | 26.2 | 27.4 | 0.51 |
| ADFI, g | 31.7 | 26.3 | 30.3 | 30.3 | 0.53 |
| Gain:Feed | 0.880 | 0.973 | 0.865 | 0.904 | 0.68 |
| Day 11-14 | | | | | |
| ADG, g | 36.0 | 34.2 | 33.8 | 36.2 | 0.56 |
| ADFI, g | 44.73 | 42.46 | 43.80 | 43.97 | 0.77 |
| Gain:Feed | 0.805 | 0.805 | 0.772 | 0.823 | 0.02 |
| Day 0-14 | | | | | |
| ADG, g | 20.2 | 19.6 | 19.1 | 20.6 | 0.49 |
| ADFI, g | 23.51 | 23.33 | 23.51 | 23.78 | 0.55 |
| Gain:Feed | 0.829 | 0.840 | 0.772 | 0.832 | 0.02 |

[1]Standard error of mean

The results demonstrate that broiler chicks fed a basal diet supplemented with 0.5% by weight American alligator serum performed better than broiler chicks fed a basal diet. For instance, over a 14 day period, broiler chicks fed a basal diet with litter supplemented with 0.5% by weight American alligator serum had an average daily weight gain that was 1.0 g more than the average daily weight gain of broiler chicks fed a basal diet with litter. Broiler chicks fed a basal diet with litter supplemented with 0.5% by weight American alligator serum had an average daily feed intake that was 0.45 g more than the average daily feed intake of broiler chicks fed a basal diet with litter.

The inventors have surprisingly and unexpectedly discovered that supplementing standard feed (starter diet) for weanling pigs (e.g., early-weaned starter pigs) or poultry hatchlings with a blood product (whole blood, hemolyzed blood, serum or plasma) from an American alligator increases both weight gain and feed intake. Supplementing the diet of weanling pigs or poultry hatchlings with whole blood, hemolyzed blood, serum, or plasma from an American alligator is expected to also enhance gut health and lessen mortality rate. Alligator serum has been shown to exhibit a broad-spectrum of antibacterial, antiviral, and antiparasitic properties. (Merchant, M, et al, 2003, Antibacterial properties of serum from the American alligator (*Alligator mississippiensis*). Comp. Biochem, Physiol. B 136(3), 505-513, incorporated herein by reference; Merchant, M, et al, 2004. Amoebacidal effects of serum from the American alligator (*Alligator mississippiensis*), J. Parasitol, 90(6): 1480-1483, incorporated herein by reference; and Merchant, M, et al, Antiviral activity of serum from the American alligator (*Alligator mississippiensis*), Antivir. Res. 66, 35-38, incorporated herein by reference).

The antibiotic properties of the alligator blood products are expected (based on the growth studies detailed above) to exhibit an antibiotic effect within the digestive system of the weanling pig or poultry hatchling to reduce the likelihood of gut related diseases and bacterial infections. Weight gain is attributable in part to a healthy digestive system and a controlled and balanced gut microflora. Therefore, the present invention may be used as a replacement for traditional subtherapeutic use of antibiotics in feed.

Other Crocodylian species have been shown to possess an innate resistance to disease indicating that the blood product from other Crocodylian species may be used as a feed supplement for weanling pigs or poultry hatchlings to increase growth and feed intake, and is expected to promote and enhance gut health. (Merchant, M., et al, 2005. Comparison of innate immune activity of all known living Crocodylian species. Comp. Biochem. Physiol. B 143, 133-137, incorporated herein by reference; Merchant M., et al, 2006. Characterization of serum compliment activity of saltwater (*Crocodylus Porosus*) and freshwater (*Crocodylus Johnsoni*) crocodiles. Comp. Biochem. Physiol. A 143, 1488-1493, incorporated herein by reference).

While preferred embodiments of the present invention have been described, it is to be understood that the embodiments described are illustrative only and that the scope of the invention is to be defined only by the appended claims when accorded a full range of equivalence, many variations and modifications naturally occurring to those skilled in the art from a perusal hereof.

What is claimed is:

1. A feed composition for a weanling pig or poultry hatchling comprising:
   a commercial feed product digestible by said weanling pig or said poultry hatchling; and
   a feed supplement, said feed supplement is a blood product from at least one Crocodylian species in an amount effective to increase weight gain of said pig or poultry hatchling being fed said feed comprising;

wherein the effective amount of the blood product to increase weight gain of the weanling pig or poultry hatchling is 0.5% to 1.0% by weight of the feed composition; and wherein said feed composition is palatable to said weanling pig or poultry hatchling.

2. The feed composition according to claim 1, wherein the effective amount of the blood product to increase weight gain of the weanling pig or poultry hatchling is 0.5% by weight of the feed composition.

3. The feed composition according to claim 1, wherein said blood product is selected from the group consisting of whole blood, hemolyzed blood, serum, and plasma.

4. The feed composition according to claim 3, wherein said whole blood, hemolyzed blood, serum, or plasma is a liquid.

5. The feed composition according to claim 3, wherein said whole blood, hemolyzed blood, serum, or plasma is a solid.

6. The feed composition according to claim 5, wherein said solid is a spray-dried, lyophilized, or granular solid.

7. The feed composition according to claim 1, wherein the Crocodylian species is selected from the group consisting of *Alligator mississippiensis, Alligator sinensis, Caiman crocodilus, Calman latirostris, Caiman yacare, Melanosuchus niger, Paleosuchus palpebrosus, Paleosuches trigonatus, Crocodylus acutus, Crocodylus cataphractus, Crocodylus intermedius, Crocodylus johnsoni, Crocodylus mindorensis, Crocodylus moreletti, Crocodylus niloticus, Crocodylus novaeguineae, Crocodylus palustris, Crocodylus porosus, Crocodylus rhombifer, Crocodylus siamensis, Osteolaemus tetraspis, Gavialis gangeticus,* and *Tomistoma schlegelii.*

8. The feed composition according to claim 1, wherein the Crocodylian species is *Alligator mississippiensis.*

* * * * *